United States Patent
Podsiadlo et al.

(10) Patent No.: US 11,760,705 B2
(45) Date of Patent: Sep. 19, 2023

(54) TRANSALKYLATION WITH REDUCED RING LOSS

(71) Applicant: ExxonMobil Chemical Patents Inc., Baytown, TX (US)

(72) Inventors: Paul Podsiadlo, Humble, TX (US); Jeffrey L. Andrews, Houston, TX (US); Michel Molinier, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 156 days.

(21) Appl. No.: 16/991,523

(22) Filed: Aug. 12, 2020

(65) Prior Publication Data

US 2021/0163379 A1 Jun. 3, 2021

Related U.S. Application Data (60) Provisional application No. 62/892,089, filed on Aug. 27, 2019.

(51) Int. Cl.
| | | |
|---|---|---|
| *C07C 6/12* | (2006.01) | |
| *C07C 7/04* | (2006.01) | |
| *C07C 7/00* | (2006.01) | |
| *C07C 5/27* | (2006.01) | |

(52) U.S. Cl.
CPC ............ *C07C 6/126* (2013.01); *C07C 5/2732* (2013.01); *C07C 7/005* (2013.01); *C07C 7/04* (2013.01)

(58) Field of Classification Search
CPC ........... C07C 6/12; C07C 6/126; C07C 7/005; C07C 7/04; C07C 5/2732; C07C 5/2737; C07C 2/54; C07C 2/64; C07C 2/66; C07C 4/08; C07C 4/12; C07C 4/14; C07C 4/18

See application file for complete search history.

(56) References Cited

U.S. PATENT DOCUMENTS

| | | | |
|---|---|---|---|
| 7,405,335 B1 | 7/2008 | Casey et al. | |
| 10,053,403 B2 | 8/2018 | Lai et al. | |
| 2007/0203376 A1 | 8/2007 | Negiz | |
| 2009/0112034 A1* | 4/2009 | Levin | ...................... C07C 6/126 585/475 |
| 2009/0234169 A1* | 9/2009 | Pelati | ...................... C07C 2/66 585/467 |

(Continued)

FOREIGN PATENT DOCUMENTS

EP 1882728 1/2008

OTHER PUBLICATIONS

Doherty et al. ("Distillation (Section 13), Perry's Chemical Engineering Handbook." McGraw-Hill Companies, Inc., New York (2008)) (Year: 2008).*

(Continued)

*Primary Examiner* — In Suck C Bullock
*Assistant Examiner* — Jason Y Chong (57) ABSTRACT

A transalkylation process co-feeds benzene at a relatively high proportion with C9+ aromatics in a feed stream to a transalkylation reactor. At lower proportions (≤5 wt %) of benzene, ring loss is greater for benzene than toluene and ring loss is increased by increasing the proportion of benzene in the feed stream. When the benzene is co-fed in a proportion sufficiently greater than 5 weight percent of the feed stream, ring loss is unexpectedly reduced.

22 Claims, 5 Drawing Sheets

(56) References Cited

U.S. PATENT DOCUMENTS

| | | | |
|---|---|---|---|
| 2015/0376086 A1* | 12/2015 | Tinger | C07C 7/005 585/314 |
| 2016/0075618 A1 | 3/2016 | Bender et al. | |
| 2016/0176787 A1 | 6/2016 | Molinier et al. | |
| 2016/0264495 A1* | 9/2016 | Molinier | B01J 19/2445 |
| 2018/0134637 A1 | 5/2018 | Lai et al. | |

OTHER PUBLICATIONS

Sinnott ("2.14 Recycle Processes." Chemical Engineering Design, Fourth ed. vol. 6, 2005, 50) (Year: 2005).*

* cited by examiner

TRANSALKYLATION WITH REDUCED RING LOSS

CROSS-REFERENCE TO RELATED APPLICATIONS

This application claims the benefit of and priority to U.S. Ser. No. 62/892,089, filed Aug. 27, 2019, which is incorporated herein by reference.

FIELD

This disclosure relates to transalkylation of aromatic hydrocarbons. In particular, this disclosure relates to transalkylation of C9+ aromatic hydrocarbons and C6/C7 aromatic hydrocarbons. This disclosure is useful, e.g., in producing xylenes such as p-xylene.

BACKGROUND

Figure 1:
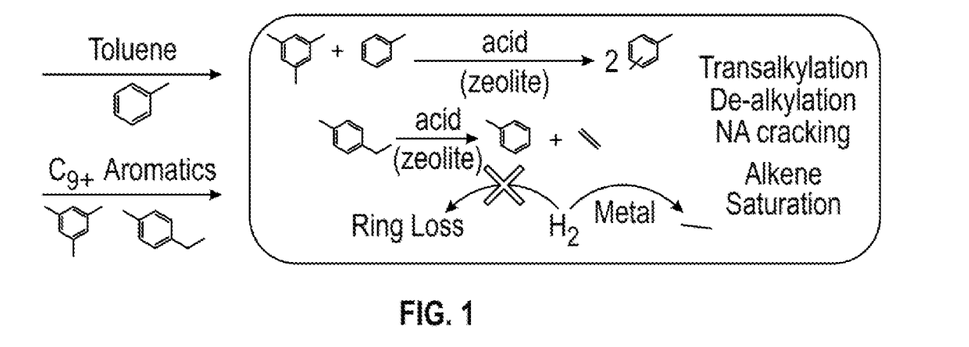
FIG. 1 is a simplified schematic showing the multifunctional nature of transalkylation catalysts and some of the main reactions.

Transalkylation of toluene and C9+ aromatics to mixed xylenes generally involves catalysts with an acid function, often from zeolite, and a metal function from one or more metals. As shown schematically in FIG. 1, in the main reactions, toluene and C9+ aromatics are transalkylated to form xylenes. However, de-alkylation and naphthene cracking also occur to produce light olefins, which must be rapidly removed to avoid forming coke and/or re-alkylating aromatics. The metal function promotes the saturation of alkenes to inert paraffins.

The metal function can also catalyze the hydrogenation of aromatic rings, causing them to lose aromaticity, which can then be followed by ring hydrocracking to convert the rings to gas. This conversion of valuable aromatic molecules, e.g., benzene, toluene, and xylenes, is often referred to as ring loss, and can substantially impact the economics of the transalkylation process.

Benzene is generally present in the toluene/C9+ aromatics feed to a transalkylation unit to some degree. It is generally accepted in the industry that benzene has a greater contribution to ring loss reactions than toluene, which in turn is greater than xylenes. Thus, it is often sought to keep benzene in the feed to a minimum, or use it sparingly only as a lesser fraction in the transalkylation feed, particularly where the process will be operated for a long period at a low weight hourly space velocity (WHSV). However, there is a cost to remove benzene from the feed stream by fractional distillation, especially where benzene is not a target product. Also, where feed is in limited supply at startup, e.g., for de-edging the catalyst, it is not desirable to further reduce the volume of the feed supply by removing benzene.

The industry is ever in search for ways to reduce the extent of ring loss in a transalkylation reactor. Moreover, the industry would be desirous of a way to reduce ring loss despite the presence of benzene in the feed, or where benzene would otherwise be a desirable feed stream component.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Applicant has discovered that co-feeding benzene in the transalkylation process, at a rate substantially higher than has been conventional, can surprisingly reduce the extent of ring loss. This was unexpected since it is generally accepted in the industry that benzene has a greater contribution to ring loss reactions than toluene, xylenes, and heavier aromatics. Co-feeding higher-than-traditional rates of benzene provides another means to limit ring loss in any transalkylation process, and may be particularly applicable where benzene is not a target product, where feed is not adequate at startup for de-edging, and/or where the process will be operated for a long period at a low weight hourly space velocity (WHSV).

According to one aspect of this disclosure, a transalkylation process comprises:
  (a) supplying a molecular hydrogen stream and a feed stream, comprising C9+ heavy aromatics and optionally further comprising toluene, to a transalkylation reactor, comprising a catalyst comprising a zeolite and at least one metal, to produce C8 aromatics; and
  (b) co-feeding benzene in the feed stream in a proportion of the feed stream sufficiently high to reduce ring loss relative to a reference stream at same transalkylation conditions of pressure, WHSV, inlet temperature, and molecular hydrogen to hydrocarbon feed ratio, where benzene in the feed stream is replaced with an equal weight of toluene in the reference stream.

DETAILED DESCRIPTION

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "an ether" include embodiments where one, two or more ethers are used, unless specified to the contrary or the context clearly indicates that only one ether is used.

For the purposes of this disclosure, the nomenclature of elements is pursuant to the version of Periodic Table of Elements as described in CHEMICAL AND ENGINEERING NEWS, 63(5), pg. 27 (1985).

Throughout the entire specification, including the claims, the following terms shall have the indicated meanings.

The term "and/or" refers to both the inclusive "and" case and the exclusive "or" case, and such term is used herein for brevity. For example, a composition comprising "A and/or B" may comprise A alone, B alone, or both A and B.

As used herein, "activation" refers to the process of making a substance chemically or catalytically reactive.

As used herein, the terms "no," "essentially no," "free of," and "essentially free of" with respect to a component of a stream or mixture mean that the component is not present, or if present is present in an amount that is no more than as a typical impurity, or no more than 5 percent by weight, preferably no more than 2 percent by weight.

The term "ring loss" is defined as the losses of aromatics from ring-opening reactions, expressed as a molar percentage of the aromatics in total feed to the transalkylation unit.

As used herein, first (reference) and second (subject) values are considered to be "substantially the same" when the second value is plus or minus no more than 5 percent of the first value; and "different" when the second value is plus or minus more than 5 percent of the first value. Similarly, transalkylation unit operating conditions are considered to be "substantially the same" when each of the feed rate taken as weight hourly space velocity (WHSV), molecular hydrogen to hydrocarbon molar ratio, reactor inlet temperature in degrees Celsius (° C.), and reactor inlet pressure, of the later operating conditions are no more than 5 percent different (plus or minus) than the earlier operating conditions; and "not substantially the same" when the difference of any of the feed rate, the molecular hydrogen to hydrocarbon molar ratio, the reactor inlet temperature, and/or reactor inlet pressure between the earlier and later operating conditions is more than 5 percent (plus or minus).

In the following discussion, reference to a carbon-containing compound such as a hydrocarbon may be made in the shorthand form of "Cn" where n refers to the number of carbon atoms in the compound regardless of the number of hydrogen atoms or heteroatoms in the compound(s). If a plus or minus sign is used, it designates a range of carbon atoms containing n carbon atoms or more or n carbon atoms or less. For example, "C9+" refers to compounds such as hydrocarbons having 9 or more carbon atoms, and "C7−" would refer to compounds such as hydrocarbons having 7 or fewer carbon atoms.

Weight hourly space velocity (WHSV), as used herein, is the mass flow rate of hydrocarbons in all feed streams to a catalytic reactor (aromatics, benzene stream, toluene stream, etc.) per mass of catalyst per hour, e.g., grams hydrocarbon/gram catalyst per hour.

As used herein, "stream" refers to process material flow in one or more pipes or channels or part(s) thereof, whether solid or fluid, including vapor, liquid, slurry, foam, mist, etc. Where a particular component is specified for a separate or isolated stream, it is understood that the stream contains at least 5 percent of that component by total weight of the stream, e.g., a "benzene stream" refers to a stream containing at least 5 percent benzene by total weight of the stream.

In embodiments according to this disclosure, co-feeding benzene results in a significant ring loss reduction, which is counter to the understanding in the art and operating experience that benzene has a higher contribution to ring loss than toluene or xylenes. Benzene is often an undesirable by-product in aromatics complexes, which are generally designed to produce xylenes, and mostly paraxylene. While some aromatics facilities may have an outlet for a benzene product, more often these are designed to minimize benzene production to the extent possible. Benzene is thus often readily available in an aromatics complex, often indefinitely, e.g., in aromatics feed from a reformer, as a by-product in a xylene isomerization unit, and/or as a by-product formed in the transalkylation process. Thus, available benzene can be fed in to the transalkylation unit to reduce ring loss.

This disclosure provides a transalkylation process comprising: (a) supplying a molecular hydrogen stream and a feed stream, comprising C9+ heavy aromatics and optionally further comprising toluene, to a transalkylation reactor, comprising a catalyst comprising a zeolite and at least one metal, to produce C8 aromatics; and (b) co-feeding benzene in the feed stream in a proportion of the feed stream sufficiently high to reduce ring loss relative to a reference stream at same transalkylation conditions of P, WHSV, inlet T, and H2:HC ratio, where benzene in the feed stream is replaced with an equal weight of toluene in the reference stream.

In any embodiment, the co-fed benzene in the feed to the transalkylation unit can be at a weight proportion in a range from greater than about 10 to about 50 percent, preferably from 15 to 30 percent of the total weight of the benzene feed stream and the C9+ aromatics feed stream. Lower rates tend to result in excessive ring loss, whereas higher rates of benzene can result in lower product yields.

In any embodiment, the co-feeding (b) can begin at a start of a catalyst cycle, e.g., following catalyst activation. Similarly, the benzene co-feeding can be used with or without catalyst sulfiding to accelerate catalyst de-edging at the start of a catalyst cycle. Also, the transalkylation reactor conditions may or may not be adjusted (with respect to production conditions) to further accelerate de-edging. At the end of the catalyst cycle, the catalyst may be removed from the TA unit and replaced with a fresh load of catalyst, which can be activated for the start of a subsequent catalyst cycle.

If desired, toluene may also be fed to the transalkylation reactor, or the feed stream can be essentially free of toluene. Where toluene and benzene are both co-fed, it is preferably at a benzene to toluene weight ratio of at least 1:1, more preferably at least 2:1, still more preferably at least 3:1, based on the total weight of benzene and toluene in all hydrocarbon feeds to the transalkylation reactor.

The TA conditions are generally effective to produce C8 aromatics and/or to convert ethylbenzene to benzene and ethane. Often, the TA conditions may comprise a weight hourly space velocity (WHSV) from 0.2 to 100 hour$^{-1}$; a molecular hydrogen to hydrocarbon molar ratio from 1 to 5; a reactor inlet temperature from 340° C. to 515° C.; a reactor inlet pressure from 0.38 to 4.24 MPa; and/or a recycle molecular hydrogen purity from 30 to 100 percent by volume, based on the total volume of the recycle molecular hydrogen. For example, the WHSV can be from 2 to 5 hour$^{-1}$; the molecular hydrogen to hydrocarbon molar ratio from 1.5 to 2; the reactor inlet temperature from 350° C. to 500° C.; the reactor inlet pressure from 2.1 to 2.5 MPa; and/or the recycle molecular hydrogen purity from 60 to 80 percent by volume, based on the total volume of the recycle molecular hydrogen.

The transalkylation process is especially applicable where the unit is operated at a relatively low WHSV for an extended period of time, and/or with a relatively high proportion of heavy aromatics in the feed to the TA unit. For example, WHSV can be less than 4 hour$^{-1}$ for a period of at least 180 days, preferably at least 365 days, more preferably at least 545 days, and still more preferably at least 730 days; and/or the total C9+ heavy aromatics in the feed stream can be 65 weight percent C9+ heavy aromatics or more, e.g., 80 weight percent C9+ heavy aromatics.

Any available benzene source can be supplied to the feed stream to the transalkylation reactor. As examples, the benzene feed stream may comprise an isomerization benzene stream from a xylene isomerization unit, preferably without extraction; a stabilizer benzene stream recycled from the transalkylation unit; a fractionation benzene stream from a feed fractionation unit; or a combination thereof.

In any embodiment, the process may further comprise recovering an effluent stream from the transalkylation unit enriched in xylenes, and treating the effluent stream in a stabilizer unit to obtain a gas stream, the stabilizer benzene stream, and a stabilizer C8+ stream. Optionally, the gas stream or a fraction thereof may be recycled to the molecular hydrogen stream to the transalkylation unit, often together with a makeup molecular hydrogen source.

The process may further comprise supplying the stabilizer C8+ stream and an aromatics feed stream to the feed fractionation unit, recovering a C8 stream from the feed fractionation unit, and recovering a paraxylene enriched product stream, a mixed xylenes stream, and optionally an isomerization benzene stream from the C8 stream. Paraxylene recovery often comprises one or more of any suitable techniques, e.g., adsorption, extraction, distillation, crystallization, and/or fractionation, or the like. The process may include feeding the mixed xylenes stream to the xylene isomerization unit to obtain a xylene isomerate stream, fractionating the xylene isomerate stream to obtain the isomerization benzene stream and an isomerization xylene stream, and supplying the isomerization xylene stream to the feed fractionation unit.

The process may further comprise recovering a C9+ aromatics fraction from the feed fractionation unit for supply to the feed stream to the transalkylation reactor, recovering the fractionation benzene stream from the feed fractionation unit, recovering a toluene stream from the feed fractionation unit, and/or optionally co-feeding the toluene from the fractionation unit to the feed stream to the transalkylation reactor.

The transalkylation process may further comprise distilling the aromatics feed stream and the stabilizer C8+ stream in at least a first column in the feed fractionation unit to obtain a C8+ bottoms stream. The toluene stream and the fractionation benzene stream can be obtained from the first column, e.g., as an overhead stream and a side draw, or a mixed benzene and toluene stream can be obtained from the first column, and fractionated to obtain the fractionation benzene stream and the toluene stream. The C8+ bottoms stream and the isomerization xylene stream can be distilled in a second column in the feed fractionation unit to obtain the C8 stream for paraxylene recovery, the C9+ aromatics fraction for transalkylation, and optionally a C11+ aromatics stream.

Figure 2:
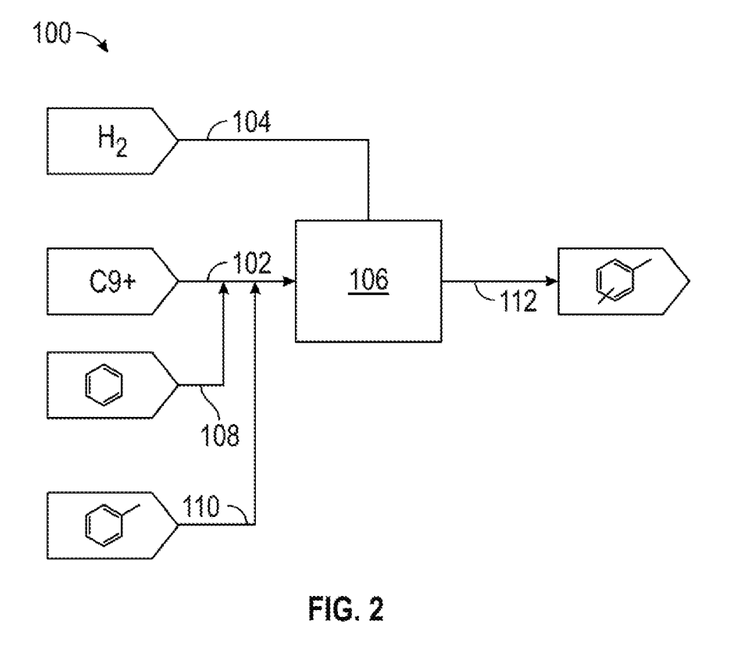
FIG. 2 is a generalized, simplified schematic flow diagram of a transalkylation process according to embodiments of this disclosure.

With reference to the drawings in which like parts and steps are identified with like numerals, FIG. 2 shows a generalized, simplified schematic flow diagram of a transalkylation process 100 according to embodiments of this disclosure. Feed stream 102 comprising C9+ heavy aromatics and molecular hydrogen stream 104 are fed to transalkylation reactor 106. Source benzene stream 108 is co-fed to the reactor 106. Source toluene stream 110 is optionally co-fed in the feed stream to the transalkylation reactor 106. The reactor 106 is loaded with a transalkylation catalyst comprising at least one metal and an acid function such as zeolite. Effluent from the reactor 106 is recovered via effluent stream 112.

Transalkylation reactors such as 106 and transalkylation catalysts are well known in the industry, and the designs and specifications are commercially available from several heavy aromatics transalkylation technology licensors. See, for example, patent documents U.S. Pat. Nos. 5,030,787, 5,942,651, 7,605,295B1, U.S. Pat. No. 8,183,424B2, U.S. Pat. No. 9,868,117B2, and US2009/0112034. The reactor 106 can be any appropriate reactor such as, for example, a radial flow, fixed bed, continuous flow, or fluid bed reactor. In any embodiment the reactor 106 can be one or a plurality of single fixed catalyst beds, or one or more multiple fixed catalyst beds. Where the reactor 106 comprises a plurality of vessels, they may be arranged for parallel and/or series flow.

In any embodiment, the catalyst can comprise zeolite and at least one metal, preferably wherein the at least one metal is a precious metal in an amount of from 0.01 wt % to 5.0 wt %, expressed as weight percentage of the precious metal based on the total weight of the catalyst composition, more preferably at least two metals on a meso-mordenite/zeolite support, and still more preferably at least one first metal of Group 10 of the IUPAC Periodic Table and at least one second metal of Groups 11-15 of the IUPAC Periodic Table, e.g., as described in patent document U.S. Ser. No. 10/053,403B2.

At the start of a transalkylation catalyst cycle, fresh catalyst is loaded in the reactor. The catalyst can be activated prior to loading, but is more commonly activated after loading, e.g., by flowing molecular hydrogen stream 104 through the reactor 106 and heating with an appropriate time and temperature profile. During activation, molecular hydrogen stream 104 is often a high-purity molecular hydrogen stream. Catalyst activation procedures are described, for example, in patent document U.S. Pat. No. 9,868,117B2.

After catalyst loading and activation, to start the catalyst cycle, flows of C9+ heavy aromatics 102 and molecular hydrogen stream 104 are often started to the reactor for a period of time effective to de-edge the catalyst. Benzene stream 108 may or may not be co-fed during the de-edging period. The de-edging is often continued until a target is met and/or for a fixed period of time, e.g., anywhere from 1 day to 6 months. The target can be an operating specification(s) indicative of sufficient de-edging, such as, for example, ring loss. For example, the de-edging period can be continued for a fixed period of time that can be shortened in the event ring loss specifications are met before then.

De-edging conditions can be substantially the same as the operating conditions as for xylene production, in terms of feed rate taken as WHSV, molecular hydrogen to hydrocarbon molar ratio, reactor inlet temperature, and/or reactor inlet pressure. Often, the relative flow rates of heavy aromatics stream 102, benzene stream 108 and toluene stream 110 can be adjusted at the transition between de-edging and production to change the C9+ conversion and/or the xylene yield. The end of the catalyst cycle can include removal of the catalyst and other turnaround operations in preparation for a new cycle start.

If desired, one or more or all of these operating conditions may be different between de-edging and normal production, e.g., to accelerate de-edging and/or to improve production for xylene yield, aromatics conversion, ring loss, benzene purity, de-ethylation of ethylbenzene, or the like.

Often, when it is desired to accelerate de-edging, it may be preferable to use a higher hydrocarbon feed rate; a lower molecular hydrogen to hydrocarbon molar ratio; a higher reactor inlet temperature; a lower reactor inlet pressure; and/or a lower recycle molecular hydrogen purity. Then, following de-edging when it is desired to improve production values such as xylene yield, aromatics conversion, ring loss, benzene purity, de-ethylation of ethylbenzene, or the like, the operating conditions for production can include a lower hydrocarbon feed rate; a higher molecular hydrogen to hydrocarbon molar ratio; a lower reactor inlet temperature; a higher reactor inlet pressure; and/or a higher recycle molecular hydrogen purity. Often, the de-edging and/or production conditions may be generally constant other than for brief periods of process upset condition or planned or unplanned shutdowns.

Figure 3:
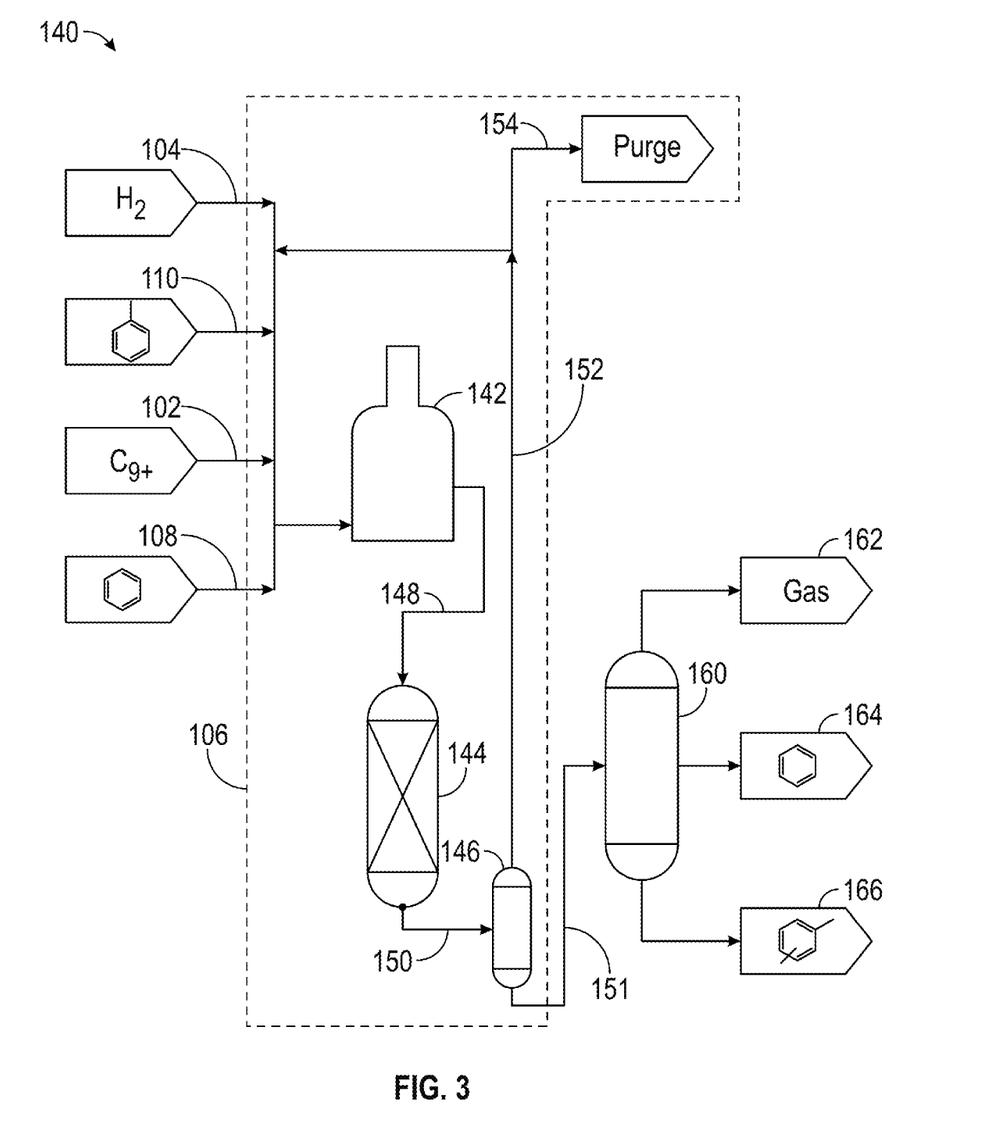
FIG. 3 is a simplified schematic flow diagram for a transalkylation process according to embodiments of this disclosure.

FIG. 3 schematically shows a simplified transalkylation process 140 according to embodiments of this disclosure. For the purposes of simplicity and clarity, FIG. 3 does not show all of the conventional pumps, heat exchangers, lines, valves, instrumentation, control systems, etc., which are familiar to those skilled in the art. In this process 140, the transalkylation unit 106 comprises fired heater 142, reactor 144, and molecular hydrogen separator 146. The feeds 102, 104, 108, and/or 110 are often combined before or after heater 142, and the heated feed mixture is supplied in line 148 to the catalytic reactor 144 for transalkylation. An effluent 150 flows to molecular hydrogen separator 146, which recovers a molecular hydrogen-rich stream 152. All or part of the stream 152 can be purged at 154, and/or all or part of the remainder can be recycled to line 148 to the reactor 144.

If desired, the process 140 can stabilize the molecular hydrogen-lean effluent in stabilizer 160 by removing light hydrocarbon gas stream 162 and optionally a benzene-rich stabilizer benzene stream 164. The stabilizer benzene stream 164 can optionally be used as benzene source stream 108 for co-feed to the feed stream 102 (see FIGS. 2 and 4) to the transalkylation reactor 144. Stabilized xylene-rich stream 166 can be further processed as desired, e.g., supplied to a fractionator in an aromatics processing unit (see FIG. 4) for xylenes recovery.

Figure 4:
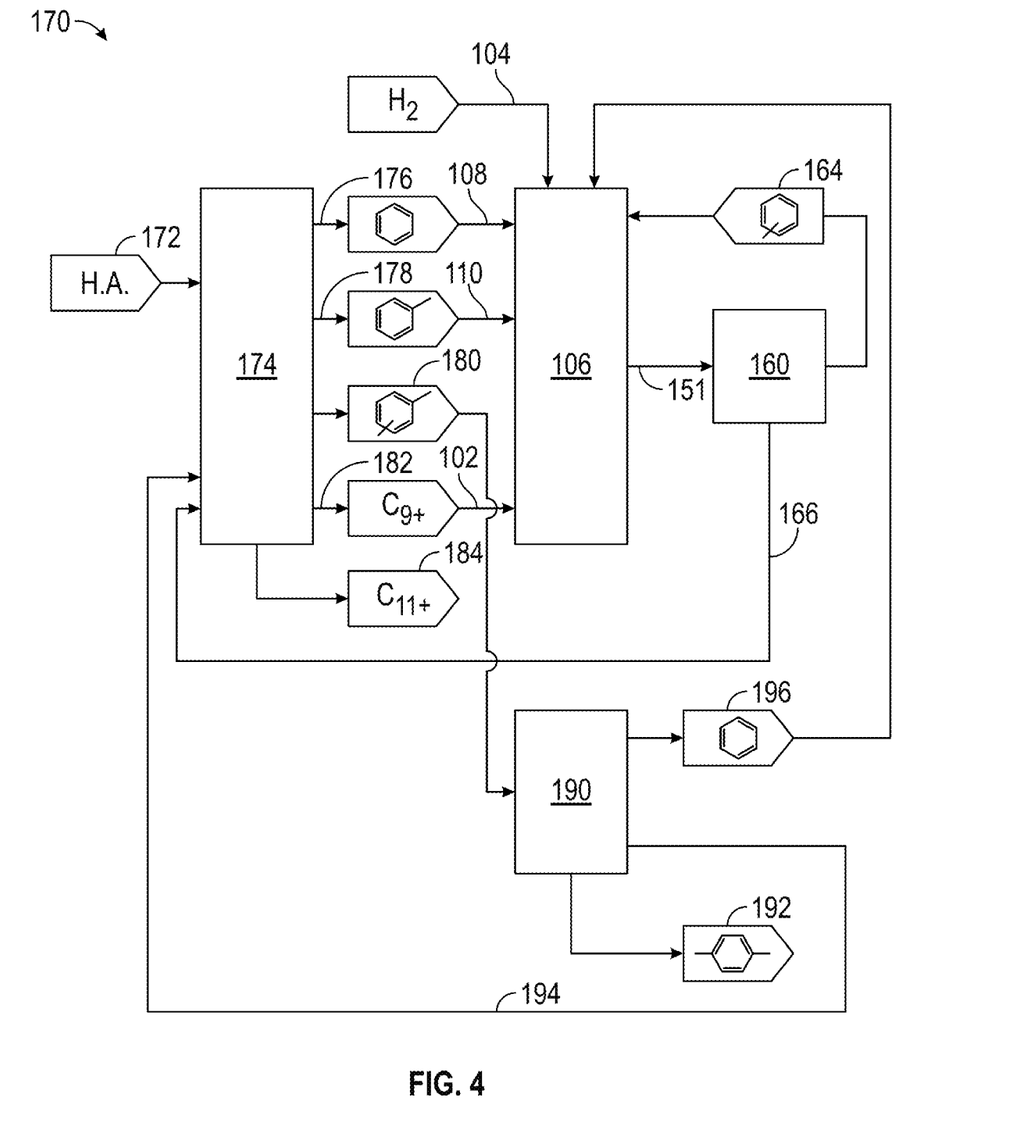
FIG. 4 is a generalized, simplified schematic flow diagram for an aromatics processing unit according to embodiments of this disclosure.

FIG. 4 is a generalized, simplified schematic flow diagram for an aromatics processing unit 170, preferably incorporating the transalkylation process 100 (FIG. 2) and/or 140 (FIG. 3), according to embodiments of this disclosure. In the processing unit 170, a heavy aromatics stream 172, preferably from a naphtha reformer in a refinery, is fed to fractionation section 174, which conventionally may include one or more distillation columns, producing a fractionation benzene stream 176, toluene fraction 178, C8 fraction 180, C9+ fraction 182, and optionally C11+ fraction 184. The heavy aromatics stream 172 could also be from another suitable source of aromatics.

Heavy aromatics stream 172 preferably contains a mixture of benzene, toluene, C8 aromatics, C9 aromatics, C10 aromatics, C11 aromatics, and/or heavier aromatics. The heavy aromatics are typically from a reformer, but this disclosure is not limited to any particular source or mixture of heavy aromatics.

Fractionation benzene stream 176 can provide a convenient source or a portion thereof for the co-fed benzene stream 108 to the transalkylation unit 106 (FIGS. 2 and/or 3). Fractionation toluene stream 178 is similarly preferably provided as the source for all or part of the toluene stream 110 fed to the transalkylation unit 106. Fractionation C9+ stream 182 can likewise serve as a source for the C9+ aromatics stream 102 to the transalkylation unit 106. C11+ aromatics stream 184, if present, can be a product stream that is exported to another processing unit or as a product stream. In any case, C9+ aromatics stream 182 can contain C11+ aromatics as desired.

The purity of the streams 176, 178, and 182 is generally not particularly critical to the extent they are fed together into the TA unit 106, provided that collectively they are desirably reasonably or preferably essentially free of C8 aromatics, which are obtained primarily as C8 stream 180. However, purity specifications may be applicable as desired for any of these streams that are exported to another process or product stream. Transalkylation unit 106 is operated as discussed in connection with FIGS. 2-3, i.e., C9+ stream 102 including stream 182 is fed to the TA unit 106 along with any co-fed benzene and/or toluene in streams 108, 110, optionally including streams 176 and/or 178, and molecular hydrogen stream 104.

Effluent stream 151 (see FIG. 3) is preferably stabilized in stabilizer 160 by purging gas, and recovering stabilizer benzene stream 164, which may optionally be co-fed to TA unit 106, as described in FIG. 3. Xylene-rich stream 166, which also typically contains unreacted and/or byproduct benzene, toluene, ethylbenzene, and other C9+ aromatics, is preferably supplied to the fractionation section, where it is separated along with heavy aromatics feed stream 172, into the various effluent streams 176, 178, 180, 182, 184.

C8 fraction 180 is preferably supplied to C8 aromatics unit 190 which may contain a paraxylene recovery unit, a xylene isomerization unit, and/or an isomerate fractionation unit, which are well known in the industry. For example, paraxylene recovery conventionally includes adsorption, extraction, distillation, crystallization, and/or fractionation, or the like to obtain paraxylene product stream 192. A paraxylene-depleted stream containing other C8 aromatics is often isomerized to obtain a C8 isomerate stream 194, which is often recycled to the fractionation section 174. If desired, an isomerization benzene stream 196 may be recovered and/or recycled to TA unit 106. As mentioned previously, the isomerization benzene stream 196 does not need high purity for recycle to the TA unit 106, and stream 196 is preferably obtained by eliminating a recrystallization step that is conventionally employed to improve the purity of the isomerization benzene stream.

Figure 5:
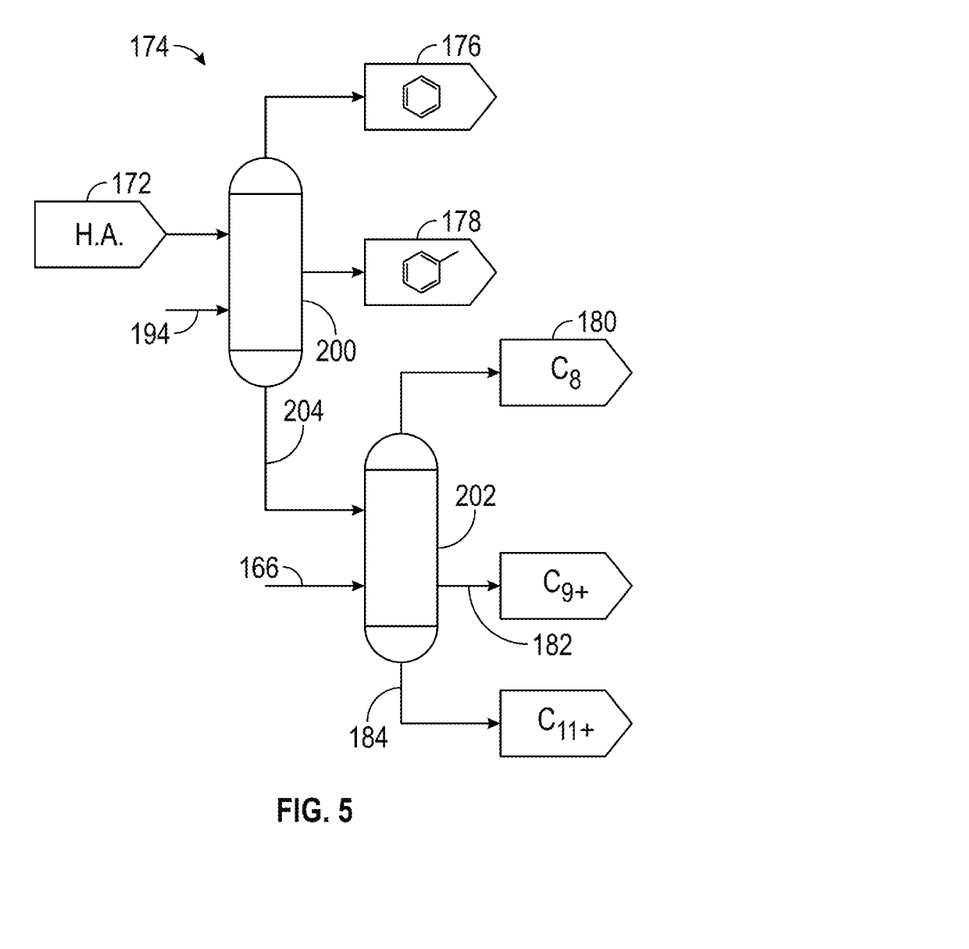
FIG. 5 is a simplified schematic flow diagram for the fractionation section of the aromatics processing unit of FIG. 4 according to embodiments of this disclosure.
Figure 6:
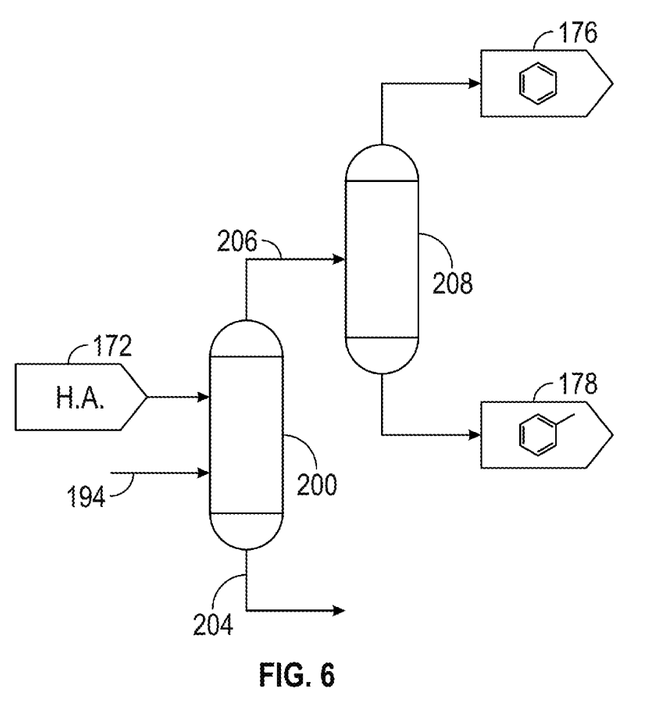
FIG. 6 is a simplified schematic flow diagram showing a mixed benzene/toluene overhead stream from the first column of the fractionation section of an aromatics processing unit according to embodiments of this disclosure.

FIG. 5 is a simplified schematic flow diagram for the fractionation section 174 of the aromatics processing unit of FIG. 4 according to embodiments of this disclosure. The fractionation section 174 shown includes a first and second columns such as reformate splitter 200 and xylenes splitter 202. The reformate splitter 200 often receives the heavy aromatics stream 172 and/or the C8 isomerate stream 194 (FIGS. 3 and 4), and produces a C8+ bottoms stream 204. Reformate benzene stream 176 and toluene stream 178 are often recovered overhead and/or as a side draw as shown, or as shown in FIG. 6, a C6/C7 overhead stream 206 can be fractionated in an auxiliary column 208 to obtain the streams 176, 178.

The xylenes splitter 202 often receives the C8+ bottoms stream 204 and/or the xylene-rich stream 166 (FIG. 5), and produces C8 aromatic stream 180 overhead and one or more C9+ aromatic bottoms and/or side draw streams 182, 184 (FIG. 5).

Embodiments

This disclosure may include one or more of the following additional embodiments:

E1. A transalkylation process comprising:
(a) supplying a molecular hydrogen stream and a feed stream, comprising C9+ heavy aromatics and optionally further comprising toluene, to a transalkylation reactor, comprising a catalyst comprising a zeolite and at least one metal, to produce C8 aromatics; and
(b) co-feeding benzene in the feed stream in a proportion of the feed stream sufficiently high to reduce ring loss relative to a reference stream at same transalkylation conditions of pressure, WHSV, inlet temperature, and molecular hydrogen to hydrocarbon molar ratio, where benzene in the feed stream is replaced with an equal weight of toluene in the reference stream.

E2. A transalkylation process comprising:
(a) supplying a molecular hydrogen stream and a feed stream, comprising C9+ heavy aromatics and optionally further comprising toluene, to a transalkylation reactor, comprising a catalyst comprising a zeolite and at least one metal, to produce C8 aromatics; and
(b) co-feeding benzene in the feed stream wherein a proportion of co-fed benzene in the feed stream is not less than 10 weight percent of the total weight of aromatics in the feed stream.

E3. The transalkylation process of E1 or E2, wherein a proportion of co-fed benzene in the feed stream is in a range from 10 to 50 weight percent, preferably from 15 to 30 weight percent of the total weight of aromatics in the feed stream E4. The transalkylation process of E1 or E2, wherein the feed stream comprises a weight ratio of benzene to toluene of at least 1:1, preferably at least 2:1, more preferably at least 3:1, based on the total weight of benzene and toluene in all hydrocarbon feeds to the transalkylation reactor.

E5. The transalkylation process of E1 or E2, wherein the feed stream is essentially free of toluene.

E6. The transalkylation process of E1 or E2, wherein the benzene co-feeding begins at a start of a catalyst cycle following catalyst activation.

E7. The transalkylation process of E1 or E2, wherein transalkylation conditions in the transalkylation reactor comprise:
a weight hourly space velocity (WHSV) from 2 to 5 hour$^{-1}$;
a molecular hydrogen to hydrocarbon molar ratio from 1.5 to 2;
a reactor inlet temperature from 350° C. to 500° C.;
a reactor inlet pressure from 2.1 to 2.5 MPa;
a recycle molecular hydrogen purity from 60 to 80 percent by volume, based on the total volume of the recycle molecular hydrogen.

E8. The transalkylation process of E1 or E2, wherein transalkylation conditions in the transalkylation reactor comprise a WHSV less than 4 hour$^{-1}$ for a period of at least 180 days.

E9. The transalkylation process of E1 or E2, wherein the feed stream to the transalkylation reactor comprises 10 weight percent or more of benzene, 65 weight percent or more of C9+ heavy aromatics, and 35 weight percent or less of toluene.

E10. The transalkylation process of E1 or E2, further comprising:
recovering an isomerization benzene stream from a xylene isomerization unit; and
supplying the isomerization benzene stream to the feed stream to the transalkylation reactor.

E11. The transalkylation process of E10, wherein the xylene isomerization unit is free of extraction, or wherein the isomerization benzene stream is recovered upstream from any extraction in the xylene isomerization unit.

E12. The transalkylation process of E1 or E2, further comprising:
recovering a xylene-rich stream from the transalkylation reactor;
treating the recovered xylene-rich stream in a stabilization unit to remove molecular hydrogen and hydrocarbons lighter than C6 from the xylene-rich stream;
recovering a benzene-rich stream from the stabilization unit; and
recycling at least a portion of the benzene-rich stream to the feed stream to the transalkylation reactor.

E13. The transalkylation process of E1 or E2, further comprising:
recovering a xylene-rich stream from the transalkylation reactor;
recovering molecular hydrogen from the xylene-rich stream; and
recycling the recovered molecular hydrogen or a fraction thereof to the molecular hydrogen stream to the transalkylation reactor.

E14. The transalkylation process of E1 or E2, further comprising:
treating an aromatics feed stream in a feed fractionation unit to recover a C9+ heavy aromatics stream and a fractionation stream enriched in benzene; and
supplying the recovered C9+ heavy aromatics stream to the feed stream to the transalkylation reactor.

E15. The transalkylation process of E14, further comprising supplying at least a fraction of the fractionation benzene stream to the feed stream to the transalkylation reactor.

E16. The transalkylation process of E14, wherein the aromatics feed stream is from a hydrocarbon reforming unit in a refinery.

E17. The transalkylation process of E14, further comprising:
recovering a xylene-rich stream from the transalkylation reactor; and
supplying at least a fraction of the xylene-rich stream to the feed fractionation unit.

E18. The transalkylation process of E17, further comprising:
recovering a C8 stream from the feed fractionation unit;
recovering a paraxylene enriched product stream and a mixed xylenes stream from the C8 stream, preferably wherein the recovery comprises adsorption, extraction, distillation, crystallization, and/or fractionation;
feeding the mixed xylenes stream to a xylene isomerization unit to obtain a xylene isomerate stream;

fractionating the xylene isomerate stream to obtain an isomerization xylene stream; and supplying the isomerization xylene stream to the feed fractionation unit.

E19. The transalkylation process of E18, further comprising:

recovering an isomerization benzene stream from the fractionation of the xylene isomerate stream; and supplying the isomerization benzene stream to the feed stream to the transalkylation reactor.

E20. The transalkylation process of E17, further comprising:

distilling the aromatics feed stream and the xylene-rich stream in a first column in the feed fractionation unit to obtain a C8+ bottoms stream and an overhead stream enriched in toluene and/or benzene;

supplying at least a fraction of the overhead stream to the feed stream to the transalkylation reactor; and distilling the C8+ bottoms stream and the isomerization xylene stream in a second column in the feed fractionation unit to obtain the C8 stream for paraxylene recovery, the C9+ aromatics fraction for transalkylation, and optionally a C11+ aromatics stream.

E21. The transalkylation process of E20, further comprising:

wherein the overhead stream is enriched in benzene; and supplying at least a fraction of the overhead stream to the feed stream to the transalkylation reactor.

E22. The transalkylation process of E21, further comprising:

recovering a toluene-enriched stream as a side draw from the first column; and supplying at least a fraction of the side draw to the feed stream to the transalkylation reactor.

E23. The transalkylation process of E20, further comprising:

wherein the overhead stream is a mixed stream of benzene and toluene; and distilling the overhead stream to obtain a fractionation benzene stream and a fractionation toluene stream.

E24. The transalkylation process of E23, further comprising:

supplying at least a portion of the fractionation benzene stream to the feed stream to the transalkylation reactor;

supplying at least a portion of the fractionation toluene stream to the feed stream to the transalkylation reactor; or supplying at least a portion of the fractionation benzene stream and at least a portion of the fractionation toluene stream to the feed stream to the transalkylation reactor.

E25. The transalkylation process of E17, further comprising:

treating the xylene-rich stream recovered from the transalkylation reactor in a stabilizer unit to obtain a gas stream, a stabilizer benzene fraction, and a stabilizer C8+ fraction;

supplying the stabilizer C8+ fraction to the feed fractionation unit; and supplying at least a portion of the stabilizer benzene enriched fraction to the feed stream to the transalkylation reactor.

Examples

This disclosure is further illustrated by the following non-limiting examples.

In the following examples, a transalkylation microunit was operated at start-of-cycle conditions while co-feeding benzene or toluene. The catalyst (Catalyst A) had two metals on a meso-mordenite/zeolite support as described in U.S. Pat. No. 10,053,403 B2. In each experiment, the catalyst was activated in situ with molecular hydrogen prior to cycle start. The catalyst and activation procedure were the same in all experiments.

Example 1. Reactor temperature 371° C. The conditions in example 1 can be deemed normal for a transalkylation process. In other words, no operating parameter in this test (WHSV, pressure, temperature, molecular hydrogen to hydrocarbon ratio) was aimed at accelerating operation severity or coke deposition on the catalyst. In experiment 1A (comparative), experiment 1B (comparative), and experiment 1C (inventive), catalyst A was tested under the same set of normal transalkylation process design conditions, except for a feed composition change; namely 20 wt % toluene in experiment 1A was replaced with 5 wt % benzene and 15 wt % toluene in experiment 1B, and with 20 wt % benzene in experiment 1C.

TABLE 1

Example 1 operating conditions

| Parameter | Experiment 1A | Experiment 1B | Experiment 1C |
|---|---|---|---|
| Catalyst system | A | A | A |
| C9+ (wt %) | 80 | 80 | 80 |
| Toluene (wt %) | 20 | 15 | 0 |
| Benzene (wt %) | 0 | 5 | 20 |
| Pressure (MPa-g (psig)) | 2.48 (360) | 2.48 (360) | 2.48 (360) |
| WHSV (hr$^{-1}$) | 3.0 | 3.0 | 3.0 |
| Reactor Temperature (° C.) | 371 | 371 | 371 |
| H2:HC molar ratio | 2.0 | 2.0 | 2.0 |
| Ring Loss (mol %) | 0.56 | 0.69 | 0.32 |

It can be seen in example 1 that replacing toluene with just 5 wt % benzene resulted in increased ring loss, whereas replacing the toluene with 20 wt % benzene unexpectedly resulted in a significant ring loss reduction from 0.56 mol % and 0.69 mol %, to just 0.32 mol %. This result is surprising in that one might have expected that feeding more benzene would result in higher ring loss, since contribution of aromatic molecules to ring loss reactions is generally understood to follow this sequence: benzene>toluene>xylenes as demonstrated in Experiments 1A and 1B.

Example 2. Reactor temperature 394° C. The conditions in example 2 can be deemed normal for a transalkylation process. In other words, no operating parameter in this test (WHSV, pressure, temperature, molecular hydrogen to hydrocarbon ratio) was aimed at accelerating operation severity or coke deposition on the catalyst. In Experiment 2A (comparative) and Experiment 2C (inventive), catalyst A was tested under the same set of normal transalkylation process design conditions, except for a feed composition change; namely 20 wt % toluene in Experiment 2A was replaced with 20 wt % benzene in Experiment 2C.

TABLE 2

Example 2 operating conditions

| Parameter | Experiment 2A | Experiment 2B | Experiment 2C |
|---|---|---|---|
| Catalyst system | A | A | A |
| C9+ (wt %) | 80 | 80 | 80 |
| Toluene (wt %) | 20 | 15 | |
| Benzene (wt %) | | 5 | 20 |
| Pressure (MPa-g (psig)) | 2.48 (360) | 2.48 (360) | 2.48 (360) |
| WHSV (hr$^{-1}$) | 3.0 | 3.0 | 3.0 |

TABLE 2-continued

Example 2 operating conditions

| Parameter | Experiment 2A | Experiment 2B | Experiment 2C |
|---|---|---|---|
| Reactor Temperature (° C.) | 394 | 394 | 394 |
| H2:HC molar ratio | 2.0 | 2.0 | 2.0 |
| Ring Loss (mol %) | 0.92 | 1.32 | 0.65 |

It can be seen that replacing 20 wt % toluene with 20 wt % benzene in Example 2 also resulted in a significant ring loss reduction from 0.92% to 0.65%, whereas 15 wt % toluene and 5 wt % benzene also resulted in increased ring loss.

In Examples 1 and 2, ring loss reduction was achieved solely by switching feed composition from 20 wt % toluene to 20 wt % benzene. There was an expectation that coke deposition would not have been accelerated in the presence of benzene vs. toluene. Therefore, this disclosure provides a means to reduce ring loss as another tool in the transalkylation operator's toolbox to reduce ring. It is applicable by default in any transalkylation unit, and can have particular applicability where there is less interest in benzene product; limited feed availability at start-up; long cycle, low WHSV, and so on.

Although only a few example embodiments have been described in detail above, those skilled in the art will readily appreciate that many modifications are possible in the example embodiments without materially departing from this disclosure. Accordingly, all such modifications are intended to be included within the scope of this disclosure as defined in the following claims. It is the express intention of the applicant not to invoke 35 U.S.C. § 112(f) for any limitations of any of the claims herein, except for those in which the claim expressly uses the words 'means for' together with an associated function and without any recitation of structure. The priority document is incorporated herein by reference.

What is claimed is:

1. A transalkylation process comprising:
(a) supplying a molecular hydrogen stream and a first feed stream, the first feed stream comprising toluene, C9+ heavy aromatics, and optionally further comprising benzene to a transalkylation reactor comprising therein a catalyst comprising a zeolite and at least one metal, to produce a first effluent comprising C8 aromatics and having a first amount of ring loss;
(b) reducing the amount of toluene in the first feed stream and co-feeding benzene or, if benzene is present in the first feed stream, increasing the amount of benzene in the first feed stream to provide a second feed stream that incudes a greater amount of benzene than the first feed stream; and
(c) supplying the molecular hydrogen stream and the second feed stream to the transalkylation reactor to produce a second effluent comprising C8 aromatics and having a second amount of ring loss, wherein the second amount of ring loss is less than the first amount of ring loss when the first feed stream and the second feed stream are processed in the transalkylation reactor at the same transalkylation conditions of pressure, WHSV, inlet temperature, and molecular hydrogen to hydrocarbon molar ratio.

2. The transalkylation process of claim 1, wherein a proportion of benzene in the second feed stream is in a range from 10 to 50 weight percent of the total weight of aromatics in the second feed stream.

3. The transalkylation process of claim 1, wherein the second feed stream comprises a weight ratio of benzene to toluene of at least 1:1, based on the total weight of benzene and toluene in all hydrocarbon feeds to the transalkylation reactor.

4. The transalkylation process of claim 1, wherein the second feed stream is essentially free of toluene.

5. The transalkylation process of claim 1, wherein the molecular hydrogen stream comprises recycle molecular hydrogen recovered from a transalkylation effluent, and wherein transalkylation conditions in the transalkylation reactor comprise:
a weight hourly space velocity (WHSV) from 2 to 5 hour$^{-1}$;
a molecular hydrogen to hydrocarbon molar ratio from 1.5 to 2;
a reactor inlet temperature from 350° C. to 500° C.;
a reactor inlet pressure from 2.1 to 2.5 MPa;
a recycle molecular hydrogen purity from 60 to 80 percent by volume, based on the total volume of the recycle molecular hydrogen.

6. The transalkylation process of claim 1, wherein transalkylation conditions in the transalkylation reactor comprise a WHSV less than 4 hour$^{-1}$ for a period of at least 180 days.

7. The transalkylation process of claim 1, wherein the second feed stream to the transalkylation reactor comprises 10 weight percent or more of benzene, 65 weight percent or more of C9+ heavy aromatics, and 35 weight percent or less of toluene.

8. The transalkylation process of claim 1, further comprising:
recovering an isomerization benzene stream from a xylene isomerization unit; and
supplying the isomerization benzene stream to the second feed stream to the transalkylation reactor, wherein the xylene isomerization unit is free of extraction, or wherein the isomerization benzene stream is recovered upstream from any extraction in the xylene isomerization unit.

9. The transalkylation process of claim 1, further comprising:
recovering a xylene-rich stream from the transalkylation reactor;
separating molecular hydrogen from the xylene-rich stream to produce a molecular hydrogen-lean effluent;
treating the molecular hydrogen-lean effluent in a stabilization unit to simultaneously remove hydrocarbons lighter than C6 and a benzene-rich stream from the molecular hydrogen-lean effluent; and
recycling at least a portion of the benzene-rich stream to the second feed stream to the transalkylation reactor.

10. The transalkylation process of claim 1, further comprising:
recovering a xylene-rich stream from the transalkylation reactor;
recovering molecular hydrogen from the xylene-rich stream; and
recycling the recovered molecular hydrogen or a fraction thereof to the molecular hydrogen stream to the transalkylation reactor.

11. The transalkylation process of claim 1, further comprising:
treating an aromatics feed stream in a feed fractionation unit to recover a C9+ heavy aromatics stream and a fractionation stream enriched in benzene; and
supplying the recovered C9+ heavy aromatics stream to the first feed stream and the second feed stream to the transalkylation reactor.

12. The transalkylation process of claim 11, further comprising supplying at least a fraction of the fractionation stream enriched in benzene to the second feed stream to the transalkylation reactor.

13. The transalkylation process of claim 11, further comprising:
recovering a xylene-rich stream from the transalkylation reactor; and
supplying at least a fraction of the xylene-rich stream to the feed fractionation unit.

14. The transalkylation process of claim 13, further comprising:
recovering a C8 stream from the feed fractionation unit;
recovering a paraxylene enriched product stream and a mixed xylenes stream from the CS stream;
feeding the mixed xylenes stream to a xylene isomerization unit to obtain a xylene isomerate stream;
fractionating the xylene isomerate stream to obtain an isomerization xylene stream; and
supplying the isomerization xylene stream to the feed fractionation unit.

15. The transalkylation process of claim 14, further comprising:
recovering an isomerization benzene stream from the fractionation of the xylene isomerate stream; and
supplying the isomerization benzene stream directly to the second feed stream to the transalkylation reactor.

16. The transalkylation process of claim 14, further comprising:
distilling the aromatics feed stream and the fraction of the xylene-rich stream in a first column in the feed fractionation unit to obtain a C8+ bottoms stream and an overhead stream enriched in toluene and/or benzene;
supplying at least a fraction of the overhead stream to at least one of the first feed stream and the second feed stream to the transalkylation reactor; and
distilling the C8+ bottoms stream and the isomerization xylene stream in a second column in the feed fractionation unit to obtain the C8 stream for paraxylene recovery, the C9+ aromatics fraction for transalkylation, and optionally a C11+ aromatics stream.

17. The transalkylation process of claim 16, wherein the overhead stream is enriched in benzene, and the process further comprises:
supplying at least a fraction of the overhead stream to the second feed stream to the transalkylation reactor;
recovering a toluene-enriched stream as a side draw from the first column; and
supplying at least a fraction of the side draw to at least one of the first feed stream and the second feed stream to the transalkylation reactor.

18. The transalkylation process of claim 16, wherein the overhead stream is a mixed stream of benzene and toluene, and the process further comprises:
distilling the overhead stream to obtain a fractionation benzene stream and a fractionation toluene stream.

19. The transalkylation process of claim 18, further comprising:
supplying at least a portion of the fractionation benzene stream to at least one of the first feed stream and the second feed stream to the transalkylation reactor;
supplying at least a portion of the fractionation toluene stream to at least one of the first feed stream and the second feed stream to the transalkylation reactor; or
supplying at least a portion of the fractionation benzene stream and at least a portion of the fractionation toluene stream to at least one of the first feed stream and the second feed stream to the transalkylation reactor.

20. The transalkylation process of claim 13, further comprising:
treating the xylene-rich stream recovered from the transalkylation reactor in a stabilizer unit to obtain a gas stream, a stabilizer benzene fraction, and a stabilizer C8+ fraction;
supplying the stabilizer C8+ fraction to the feed fractionation unit; and
supplying at least a portion of the stabilizer benzene enriched fraction to the second feed stream to the transalkylation reactor.

21. The transalkylation process of claim 1, wherein a total amount of hydrocarbons in the first feed stream introduced into the transalkylation reactor consists of the toluene, the C9+ heavy aromatics, and, if present, the optional benzene, and wherein a total amount of hydrocarbons in the second feed stream introduced into the transalkylation reactor consists of the C9+ heavy aromatics, the benzene, and, if present, toluene.

22. A transalkylation process comprising:
(a) supplying a molecular hydrogen stream and a first feed stream, the first feed stream comprising toluene, C9+ heavy aromatics, and optionally further comprising benzene to a transalkylation reactor comprising therein a catalyst comprising a zeolite and at least one metal, to produce a first effluent comprising C8 aromatics and having a first amount of ring loss; and
(b) reducing the amount of toluene in the first feed stream and co-feeding benzene or, if benzene is present in the first feed stream, increasing the amount of benzene in the first feed stream to provide a second feed stream that includes a greater amount of benzene than the first feed stream,
(c) supplying the molecular hydrogen stream and the second feed stream to the transalkylation reactor to produce a second effluent comprising C8 aromatics and having a second amount of ring loss, wherein the first feed stream and the second feed stream are processed in the transalkylation reactor at same transalkylation conditions of pressure, WHSV, inlet temperature, and molecular hydrogen to hydrocarbon molar ratio, and wherein the second amount of ring loss is less than the first amount of ring loss.

* * * * *